United States Patent
Hatakeda et al.

(10) Patent No.: US 7,071,350 B2
(45) Date of Patent: Jul. 4, 2006

(54) METHOD OF INTRODUCING AMINO GROUP AND METHOD OF SYNTHESIZING AMINO ACID COMPOUND

(75) Inventors: Kiyotaka Hatakeda, Miyagi (JP); Osamu Sato, Miyagi (JP); Mitsuhiro Kanakubo, Miyagi (JP); Yutaka Ikushima, Miyagi (JP); Kazuo Torii, Miyagi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 43 days.

(21) Appl. No.: 10/450,157

(22) PCT Filed: Oct. 30, 2001

(86) PCT No.: PCT/JP01/09498

§ 371 (c)(1),
(2), (4) Date: Jun. 11, 2003

(87) PCT Pub. No.: WO02/48091

PCT Pub. Date: Jun. 20, 2002

(65) Prior Publication Data

US 2004/0162434 A1  Aug. 19, 2004

(30) Foreign Application Priority Data

Dec. 11, 2000 (JP) .................................. 2000-376469

(51) Int. Cl.
*C07C 61/00* (2006.01)
*C07C 229/00* (2006.01)
*C07C 205/00* (2006.01)

(52) U.S. Cl. .............. 560/155; 562/400; 562/444; 562/553

(58) Field of Classification Search ............. 560/155; 562/400, 444, 553

See application file for complete search history.

(56) References Cited

U.S. PATENT DOCUMENTS 2,734,081 A  2/1956  Boatright .................... 562/576
4,350,826 A  9/1982  Edwards et al. ............ 562/444

FOREIGN PATENT DOCUMENTS

JP  5-201940  8/1993
JP  6-271518  9/1994
JP  6-329605  11/1994

*Primary Examiner*—Cecilia J. Tsang
*Assistant Examiner*—Taylor Victor Oh
(74) *Attorney, Agent, or Firm*—Oblon, Spivak, McClelland, Maier & Neustadt, P.C.

(57) ABSTRACT

The present invention relates to a method for introducing an amino group into an organic acid or an organic ester by reacting an organic salt or an organic ester and ammonia under high-temperature and high-pressure water conditions, a method for synthesizing an amino acid or an amino ester by the above method, and a method for manufacturing an amino acid compound by synthesizing an amino acid or an amino ester by the above method and separating and refining it with an ion exchange resin.

18 Claims, 3 Drawing Sheets

METHOD OF INTRODUCING AMINO GROUP AND METHOD OF SYNTHESIZING AMINO ACID COMPOUND

TECHNICAL FIELD

This invention relates to a method for introducing an amino group into an organic acid or an organic ester under high pressure and high temperature, and more particularly relates to a method for introducing an amino group into an organic acid and an organic ester by reacting an organic salt or an organic ester with ammonia or an ammonium salt compound under high-temperature and high-pressure water conditions, and to a method for synthesizing or manufacturing an amino acid compound from an organic salt or an organic ester by the above method.

The present invention makes it possible to synthesize or manufacture an amino acid compound under high temperature and pressure, either continuously or in batches, using an organic salt or an organic ester and ammonia or an ammonium salt compound as the reaction substrates, and without involving an organic solvent or catalyst in the synthesis process, and as such provides a favorable and useful method for industrial purposes.

BACKGROUND ART

Amino acid compounds have generally been manufactured in the past by many different methods such as fermentation, hydrolysis, and organic synthesis. Alanine, for instance, has been synthesized by microbial fermentation or by utilizing a hydrolyzate thereof, and has also been produced by organic synthesis processes in which organic reagents are used.

The following are typical examples of conventional alanine synthesis.

a) Alanine synthesis by electrical oxidation of 3-amino-1-propanol in sulfuric acid using palladium electrodes Reference 1: Jubilee Vol. Emil Barell, 1946, 85–91 b) Alanine synthesis from ethylenecyanohydrin

Reference 2: Boatright, U.S. Pat. No. 2,734,081 (1956 to Am. Cyanamid)

c) Alanine synthesis from methylaldehyde

Reference 3: E. C. Kendall & B. F. McKenzie, Org. Synth., 1, 21 (1941)

Reference 4: R. Draudry, Can. J. Res., 26B, 773 (1948)

d) β-Alanine synthesis from β-propiolactone

Reference 5: Ford, Org. Sys. Coll. Vol. 3, 34 (1955)

These and other methods that involve the use of electrode synthesis with a catalyst or ordinary synthesis have been employed.

Of the above methods, the Strecker method used in the synthesis of Reference 3, for example, has a long history as a method for synthesizing α-amino acids, but its great versatility still makes it useful. With this method, an aldehyde is reacted first with ammonia and then with hydrogen cyanide, and the intermediate product thus obtained is hydrolyzed with an acid or alkali to synthesize an α-amino acid with one extra carbon. In Reference 4, which makes use of the Bucherer method (which is an improved version of the above), alanine is synthesized using an alkali cyanide and ammonium carbonate. Since these two synthesis methods generate highly toxic hydrogen cyanide, they are considered to require the utmost caution (Shin Jikken Kagaku Koza [New Experimental Chemistry Lectures] 14, Synthesis and Reaction of Organic Compounds, Part 3, pp. 1673–1675, Maruzen (1978)]. Also, β-alanine has been synthesized by reacting β-propiolactone with ammonia in an acetonitrile solvent (Reference 5).

Thus, numerous factors have to be taken into account with conventional chemical synthesis methods, such as the disposal of organic solvents and toxic substrate substances used in the synthesis reaction, disposal of used catalysts, the danger to humans posed by by-products, and the safe usage of these substances. Also, the larger is the scale of this synthesis, the more serious these considerations become. Therefore, there is a need for the development of technology for disposing of used toxic substrate substances, organic solvents, catalysts, and so forth. Accordingly, the basic problems outlined above could be solved if some completely new synthesis method that did not involve the use of these toxic substrate substances, organic solvents, catalysts, and so forth could be developed.

In light of this situation, and in view of the prior art discussed above, the inventors conducted research into a method for introducing an amino group into an organic acid or an organic ester under high temperature and pressure, whereupon they discovered that an amino group can be introduced into an organic acid or organic ester by reacting an organic salt or an organic ester and ammonia or an ammonium salt compound under high-temperature and high-pressure water conditions, and perfected the present invention upon conducting follow-up research based on this finding.

The present invention provides a method for introducing an amino group, a method for synthesizing an amino acid compound, and a method for manufacturing an amino acid compound, all under high-temperature and high-pressure water conditions.

The present invention is a method for introducing an amino group, wherein an amino group is introduced into an organic acid or an organic ester by reacting an organic salt or an organic ester with ammonia under high-temperature and high-pressure water conditions; a method for synthesizing an amino acid compound, wherein an organic salt or an organic ester is reacted with ammonia under high-temperature and high-pressure water conditions, and an amino group is introduced into the organic acid or the organic ester, thereby synthesizing an amino acid or an amino ester; and a method for manufacturing an amino acid compound, wherein an organic salt or an organic ester is reacted with ammonia under high-temperature and high-pressure water conditions, an amino group is introduced into the organic acid or organic ester to synthesize an amino acid or an amino ester, and this product is then separated and refined with an ion exchange resin.

DISCLOSURE OF THE INVENTION

Specifically, it is an object of the present invention to provide a novel method for introducing an amino group, in which the amino group is introduced by reacting an organic salt or an organic ester with ammonia or an ammonium salt compound under high-temperature and high-pressure water conditions.

It is a further object of the present invention to provide a novel method for synthesizing an amino acid compound, in which an amino acid or an amino ester is synthesized by the above-mentioned amino group introduction method from an organic salt or an organic ester and ammonia or an ammonium salt compound.

It is a further object of the present invention to provide a novel method for synthesizing an amino acid by the above-mentioned amino group introduction method, such as synthesizing alanine from a hydroxy salt type of sodium lactate and ammonia or an ammonium salt, glycine from a glycolate, aspartic acid from a malate, α,β-diaminosuccinic acid from a tartrate, 4-amino-n-butyric acid from sodium 4-hydroxy-n-butyrate, or a 3-amino-n-butyric ester from a 3-hydroxy-n-butyric ester.

It is a further object of the present invention to provide a method for synthesizing an amino acid compound by batch process in which an organic salt or an organic ester and ammonia or an ammonium salt compound are introduced into a reactor under high-temperature and high-pressure water conditions, or a continuous method for synthesizing an amino acid in which an amino acid compound is continuously synthesized.

It is a further object of the present invention to provide a method for manufacturing a high-purity amino acid compound, wherein an amino acid or an amino ester is synthesized from an organic salt or an organic ester and ammonia or an ammonium salt compound by the above-mentioned amino group introduction method, and the amino acid compound is separated and refined from the resulting reaction solution by using an ion exchange resin.

To solve the above problems, the present invention is constituted by the following technological means.

(1) A method for introducing an amino group into an organic acid or an organic ester comprising reacting an organic salt or an organic ester with ammonia or an ammonium salt compound under high-temperature and high-pressure water conditions.

(2) A method for synthesizing an amino acid compound comprising reacting an organic salt or an organic ester with ammonia or an ammonium salt compound under high-temperature and high-pressure water conditions to introduce an amino group into the organic acid or the organic ester, and obtaining an amino acid or an amino ester.

(3) The method for synthesizing an amino acid compound according to (2) above, wherein an organic acid or an organic ester is reacted with ammonia or an ammonium salt compound under high-temperature and high-pressure water conditions of that the temperature is at least 250° C. and the pressure is at least 20 MPa.

(4) The method for synthesizing an amino acid compound according to (2) or (3) above, wherein an organic salt or an organic ester is reacted with aqueous ammonia, ammonium carbonate, or ammonium acetate under high-temperature and high-pressure water conditions.

(5) The method for synthesizing an amino acid compound according to one of (2) to (4) above, wherein a hydroxy salt or a hydroxy ester is used as the organic salt or organic ester.

(6) The method for synthesizing an amino acid compound according to one of (2) to (5) above, wherein a sodium salt, potassium salt, or ester compound of lactic acid, glycolic acid, malic acid, tartaric acid, 3-hydroxy-n-butyric acid, or 4-hydroxy-n-butyric acid is used as the organic salt or organic ester.

(7) The method for synthesizing an amino acid compound according to one of (2) to (6) above, wherein an organic salt or an organic ester and ammonia or an ammonium salt compound are introduced into a reactor and continuously reacted under high-temperature and high-pressure water conditions.

(8) A method for manufacturing an amino acid compound using an organic salt or an organic ester and ammonia or an ammonium salt compound as the reaction substrates under high-temperature and high-pressure water conditions comprising introducing the organic salt or organic ester and the ammonia or ammonium salt compound into a reactor, reacting them continuously under high-temperature and high-pressure water conditions, and then subjecting the reaction solution thus obtained to an ion exchange resin to obtain a separated and refined amino acid.

The present invention will now be described in further detail.

To facilitate an understanding of the present invention, the following detailed description is of a case in which ammonia or an ammonium salt compound is reacted under high temperature and pressure with a corresponding hydroxy salt or hydroxy ester to synthesize alanine, glycine, or 4-amino-n-butyric acid as amino acids, or 3-amino-n-butyric ethyl ester as an amino acid derivative, but the present invention is not limited to or by these examples.

A typical example of the synthesis method of the present invention, which the inventors developed through various experiments, is a method in which alanine is synthesized by introducing a sodium lactate aqueous solution and an ammonia aqueous solution, an ammonium carbonate aqueous solution, or an ammonium actetate aqueous solution into a reactor under high-temperature and high-pressure water conditions, and passing these compounds through the reactor at high speed. The raw material reagents used in the synthesis method of the present invention are just an organic salt or an organic ester and ammonia or an ammonium salt compound. Water under high temperature and high pressure is used as a reaction solvent or reaction site in the present invention, and no organic solvent or catalyst is used, nor is there any particular need to use these. Therefore, when this method is used, there is substantially no discharge of wastes that would have to be disposed of, such as toxic gas, waste solvent, or spent catalyst. Also, any unreacted organic salt, organic ester, ammonia, or ammonium compound, as well as the used water, can be reused in the reaction of the present invention. Further, since the method of the present invention allows useful amino acid compound products, such as amino acids or derivatives thereof, to be synthesized continuously and at high speed, it is believed to be an ideal method for manufacturing these products. This reaction can also be carried out in a batch reactor.

The amino group introduction method and amino acid compound synthesis method of the present invention will now be described in detail.

With the present invention, an amino acid or an amino ester can be synthesized by reacting a hydroxy salt or hydroxy ester and ammonia or an ammonium salt compound under high-temperature and high-pressure water conditions, and introducing an amino group into the hydroxy acid or hydroxy ester.

In general, amino acids are produced mainly by living organisms, but can also be manufactured by organic synthesis. In the case of alanine, for instance, the Strecker method can be employed to react methylaldehyde first with ammonia, and then with hydrogen cyanide, and the intermediate product thus obtained is hydrolyzed with an acid or alkali to synthesize an α-amino acid with one extra carbon. In the Bucherer method, which is an improved version of the above, alanine is obtained by reacting an alkali cyanide and ammonium carbonate with methylaldehyde. Unfortunately, both of these methods generate highly toxic hydrogen cyanide, so they are considered to require the utmost caution.

In contrast, the inventors discovered that alanine, glycine, aspartic acid, α,β-diaminosuccinic acid, 4-amino-n-butyric acid, 3-amino-n-butyric ethyl ester, and other such amino acids and derivatives thereof can be synthesized by reacting an organic salt or an organic ester, such as sodium lactate, sodium glycolate, sodium malate, sodium potassium tartrate, sodium 4-hydroxybutyrate, ethyl 3-hydroxy-n-butyrate, or the like, respectively, with ammonia or an ammonium salt compound.

The synthesis reaction formulas for alanine, glycine, 4-amino-n-butyric acid, and 3-amino-n-butyric ethyl ester are given below as specific examples of the amino acid synthesis pertaining to the present invention.

[First Chemical Formula]

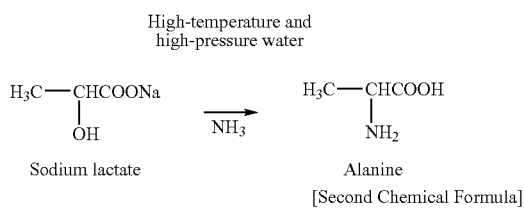

[Second Chemical Formula]

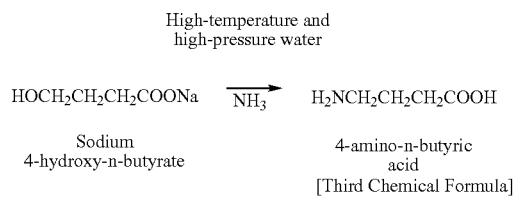

[Third Chemical Formula]

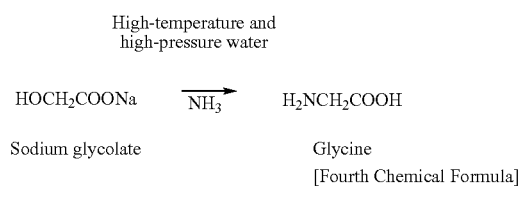

[Fourth Chemical Formula]

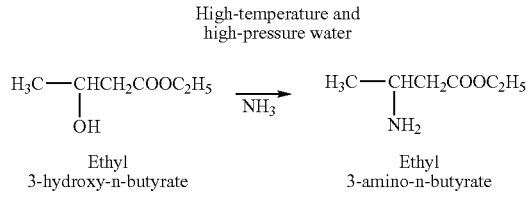

The temperature of the high-temperature and high-pressure water can be controlled from outside the reactor by using a heater, a molten salt, or the like. The temperature can also be controlled by an endothermic approach within the reactor. High-temperature and high-pressure water can also be manufactured ahead of time and injected into the reactor from the outside. It is also possible to control the reaction conditions by supplying two or more types of high-temperature and high-pressure water under different temperature and pressure conditions to the reactor. The pressure inside the reaction vessel can be controlled with a pressure regulator valve if the reactor has a flow design. As to the reaction pressure in a batch process, the spontaneous pressure at the usage temperature can be calculated, for example. Furthermore, the pressure can be controlled by injecting nitrogen gas or another vapor. It is generally best for the pressure to be no lower than the spontaneous pressure at the usage temperature.

Basically, the present invention is achieved under high-temperature and high-pressure water conditions in which the temperature is at least 250° C. and the pressure is at least 20 MPa. The present invention can be achieved even more preferably under high-temperature and high-pressure water conditions in which the temperature is at least 300° C. and the pressure is at least 25 MPa. Furthermore, the present invention will be achieved most favorably if the high-temperature and high-pressure water conditions are selected so that the temperature is between 300 and 420° C. and the pressure is between 25 and 50 MPa. The ideal temperature conditions will vary with the treatment time, but can generally be selected favorably from a temperature range of 250 to 450° C. The suitable temperature and pressure conditions can be selected as dictated by the treatment quantity and the reaction apparatus.

A high-temperature and high-pressure reaction apparatus can be used, for example, but the type of reaction apparatus is not limited, as long as it is one that allows the reaction conditions to be set to high-temperature and high-pressure water conditions.

Examples of a favorable reaction apparatus include the batch reaction apparatus and the flow high-temperature and high-pressure reaction apparatus used in the present invention. A commercially available autoclave can be used favorably.

The reaction conditions will vary with the type and concentration of the organic salt or organic ester being used, the type and concentration of the ammonia or ammonium salt compound, the reaction time, and the high-temperature and high-pressure water conditions.

With the present invention, examples of the organic salt or organic ester serving as the reaction substrate include sodium and potassium salts of 4-hydroxy-n-butyric acid, lactic acid, glycolic acid, malic acid, tartaric acid, 4-hydroxy-n-butyric acid, 3-hydroxy-n-butyric acid, 2-hydroxy-3-methylbutyl acid, citric acid, glyceric acid, tropic acid, benzylic acid, and hydroxyvaleric acid, as well as esters of these. Other examples include salts and esters of hydroxy acids having at least one carboxyl group and at least one hydroxyl group per molecule. As for hydroxy acids, salts and esters of α-hydroxy acids, β-hydroxy acids, γ-hydroxy acids, δ-hydroxy acids, ε-hydroxy acids, and so forth can all be used favorably in the reaction. Sodium salts, potassium salts, calcium salts, magnesium salts, and other such alkali salts or alkali metal salts can all be used favorable as the above-mentioned salts of organic acids.

Methyl esters, ethyl esters, butyl esters, heptyl esters, hexyl esters, and other such alkyl esters can be used favorably as the above-mentioned ester, but the present invention is not limited to these, and any ester compound can be used.

The organic salt and organic ester used in the reaction of the present invention is not limited to a single type, and the reaction will also proceed favorably when a mixture of two or more types is used. Hydroxycarboxylic acids such as aliphatic saturated hydroxycarboxylic acids, aliphatic unsaturated hydroxycarboxylic acids, and mandelic acid and other such aromatic hydroxycarboxylic acids, steroids, and other such organic salts and organic esters can all be used favorably as the reaction substrate in the present invention.

When a flow type of apparatus is used, the concentration in which the organic salt or organic ester is introduced into the reactor can be controlled, for example, by controlling the flux of the high-temperature and high-pressure water used as the carrier water or the introduction flux of the organic salt or organic ester serving as the reaction substrate. The organic salt or organic ester and the ammonia or ammonium salt compound can be supplied simultaneously or individually, and may be supplied to the reaction after first being dissolved in carrier water. The concentration in which the organic salt or organic ester is introduced into the reactor can usually be selected from a range of 1 mM to 10 M. Preferably, a suitable concentration is selected from a range of 5 mM to 5 M, and ideally a suitable concentration is selected from a range of 10 mM to 2 M, but the present invention is not limited to these concentration values. With a batch process, the concentration of the supplied organic salt or organic ester just needs to be controlled. The concentration of the organic salt or organic ester within the reactor will vary with the density of the high-temperature and high-pressure water participating in the reaction.

With the present invention, the quantity of amino groups introduced, the position where the amino groups are introduced, the type of amino acid compound produced, the production amount, and the reaction yield can be manipulated by adjusting the temperature and pressure of the reaction system, the reaction time, the concentration of the reaction substrate, and the concentration of the ammonia or ammonium salt, according to the type of organic salt or organic ester in question.

Aqueous ammonia with a concentration of 28% can usually be used favorably in the reaction, but the reaction will still proceed if gaseous ammonia is introduced into the high-temperature and high-pressure water. Ammonium salt compounds that can be used favorably include ammonium carbonate, ammonium acetate, ammonium formate, ammonium chloride, and ammonium sulfate.

In most cases, the ammonia or ammonium salt compound is introduced into the reactor after being mixed with the organic salt or organic ester serving as the reaction substrate. Here, the ammonia or ammonium salt compound is usually used in the form of an aqueous solution, and the reaction concentration can be suitably selected from a range of 1 to 20 times the organic salt or organic ester concentration. For instance, the concentration of an ammonia aqueous solution or ammonium aqueous solution can be selected from a range of 1 mM to 20 M, and preferably 5 mM to 10 M. The best range is from 10 mM to 8 M, but the present invention is not limited to these concentration values. The reaction of the present invention will proceed whether the organic salt or organic ester and the ammonia or ammonium salt compound are introduced separately into the reactor, or are used after being directly mixed in carrier water. The reaction of the present invention can also be achieved by using a mixture of ammonia and an ammonium salt.

In the reaction system of the present invention, an organic salt or an organic ester and ammonia or an ammonium salt compound serving as the reaction substrates should be present in high-temperature and high-pressure water with a temperature of at least 250° C. and a pressure of at least 20 MPa, but there is no particular need to add a water-soluble catalyst such as metal ions, an acid, or a base, or an ionic fluid, or a metal-supported catalyst, a solid acid, a solid base, or another such solid catalyst, or an enzyme, or the like, nor is there any need to use an organic solvent.

The present invention is basically characterized in that the above-mentioned reaction substrates are made to be present in high-temperature and high-pressure water, and the organic salt or organic ester and the ammonia or ammonium salt compound are reacted in the absence of a catalyst, or without the participation of an organic solvent in the reaction, so that an amino group is introduced into the organic acid or organic ester, and in that this synthesizes an amino acid compound, but if needed, there is no problem whatsoever with adding and reacting methanol, ethanol, ethylene glycol, or another such water-soluble organic solvent, metal ions, an acid, a base, or another such water-soluble catalyst, an ionic fluid, or a metal-supported catalyst, a solid acid, a solid base, or another such solid catalyst, or an enzyme.

With the present invention, the above-mentioned reaction system results in an amino group being introduced into the organic acid or organic ester, or an amino acid compound being synthesized, in a very short reaction time of about 0.001 second to 10 minutes. For example, when a flow type of reaction apparatus is used, the reaction time can be controlled by controlling the reaction temperature, reaction pressure, flow rate of the high-temperature and high-pressure water, introduction rate of the reaction substrate, size of the reactor, length of the flow passages in the reactor, and other such factors. Preferably, the reaction time is selected from a range of 0.01 second to 5 minutes, and even more preferably from a range of 0.03 second to 3 minutes, with the best range being from 0.03 second to 1 minute, but the present invention is not limited to these values.

As shown in the examples given below, the inventors have used a high performance liquid chromatography/mass spectroscopy apparatus (LC-MS apparatus) and a Fourier infrared spectrophotometer (FTIR apparatus) to confirm that an amino group can be introduced into an organic acid or an organic ester in a short time (such as a reaction time of about 0.2 second) under high-temperature and high-pressure water conditions. Furthermore, they used an LC-MS apparatus to isolate and identify the types of organic salt, organic acid, organic ester, and amino acid, and to accurately quantify the amounts thereof contained. They also used an ion exchange resin and the like to separate and refine a continuously obtained amino acid compound, measured the infrared absorption spectrum with an FTIR apparatus, and compared this spectrum with that of a reagent chemicals of high purity, which afforded accurate identification of the type of amino acid compound. Similarly, the type and purity of an amino acid compound can be confirmed by NMR measurement.

For example, alanine with a concentration of 0.7 to 6.9 mM was synthesized from aqueous ammonia and sodium lactate with a concentration of 0.181 M to 0.555 M using a flow type of apparatus at 300 to 400° C., a pressure of 30 MPa, and a reaction time of 0.10 to 0.38 second. In this reaction, it was confirmed that the sodium lactate underwent ion exchange and was converted into lactic acid. Also, ethyl 3-aminobutyrate with a concentration of 3.3 mM was synthesized from aqueous ammonia and ethyl 3-hydroxy-n-butyrate with a concentration of 0.241 M using the same flow apparatus and at a temperature of 374° C., a pressure of 30 MPa, and a reaction time of 0.20 second. Similarly, in a batch process, alanine with a concentration of 12.8 mM was synthesized from aqueous ammonia and sodium lactate at a temperature of 350° C., a pressure of 30 MPa, and a reaction time of 40 seconds. As a result of these reactions, the ammonia or ammonium compound reacted with the hydroxyl groups in the organic ester or the organic acid changed from the above-mentioned organic salt, and amino groups were introduced at the positions of these hydroxyl groups, which was confirmed with an LC-MS apparatus, an NMR measurement apparatus, and an FTIR apparatus. By-product water is believed to accompany the introduction of amino groups.

The reaction yield of the amino acid compound produced with the present invention varies with the temperature, pressure, reaction time, and other reaction conditions, the type of organic salt or organic ester, the concentration of the organic salt or organic ester, the concentration of the ammonia or ammonium compound, the configuration of the reaction apparatus, the size of the reactor, and other such factors. For instance, the reaction yield was from 1.1% to 2.5% when aspartic acid was synthesized using a flow apparatus. This aspartic acid was recovered as a mixture with the raw material malic acid and so forth. Similarly, many types of amino acid compound are recovered along with the raw material substrates from various organic salts, organic acids, or organic esters or mixtures of these, but the amino acid compound can be separated and refined from the raw material substrates by treating the reaction solution obtained after the reaction with an ion exchange resin, such as a cation exchange resin, an anion exchange resin, or a mixture of these. Furthermore, since the amino acid compounds can be separated from one another, each type of amino acid compound can be refined and concentrated. Also, the organic salt, organic acid, or organic ester recovered at the same time can be reused as raw material. Ordinary, commercially available amino acid separating materials that are made from zeolite, reversed phase silica gel, alumina, cellulose powder, activated carbon, or the like can also be utilized instead of an ion exchange resin.

Therefore, a high-purity amino acid compound can be favorably manufactured by reacting an organic salt or an organic ester and ammonia or an ammonium salt compound under high-temperature and high-pressure water conditions to synthesize an amino acid or an amino ester, and then refining out the amino acid or amino ester from the obtained reaction solution using an ion exchange resin, zeolite, reversed phase silica gel, alumina, cellulose powder, or another standard material for separating amino acids.

With the present invention, having an organic salt or an organic ester and ammonia or an ammonium salt compound be present in a specific concentration as reaction substrates in hot water under high-temperature and high-pressure water conditions allows, for example, 4-amino-n-butyric acid to be synthesized from a hydroxy ester type of sodium 4-hydroxybutyrate and ammonia, or ethyl 3-amino-n-butyrate from ethyl 3-hydroxybutyrate. In this case, if salts of lactic acid, glycolic acid, malic acid, and tartaric acid are reacted instead of sodium 4-hydroxy-n-butyrate with ammonia or an ammonium salt compound, an amino group will be introduced into these organic acids, synthesizing alanine, glycine, aspartic acid, or α,β-diaminosuccinic acid. An organic salt is usually converted into an organic acid during the reaction. Also, continuously introducing an organic salt or an organic ester and an ammonia aqueous solution or an ammonium salt compound into the reactor allows various types of amino acids and amino esters corresponding to the respective organic salts or organic esters to be synthesized continuously.

The above makes it clear that with the present invention, an amino group can be introduced into an organic acid or organic ester by adjusting the reaction conditions in the above-mentioned reaction system, the type of organic salt or organic ester serving as the reaction substrate, and the concentration of the organic salt or organic ester and the ammonia aqueous solution or ammonium salt compound, and that this allows an amino acid or an amino ester to be synthesized in a short time, which means that the present invention is useful as a novel method for introducing amino groups, method for synthesizing amino acid compounds, and method for manufacturing amino acid compounds.

BEST MODE FOR CARRYING OUT THE INVENTION

The present invention will now be described in specific terms through examples, but the present invention is not limited in any way by the following examples.

EXAMPLE 1

Figure 1:
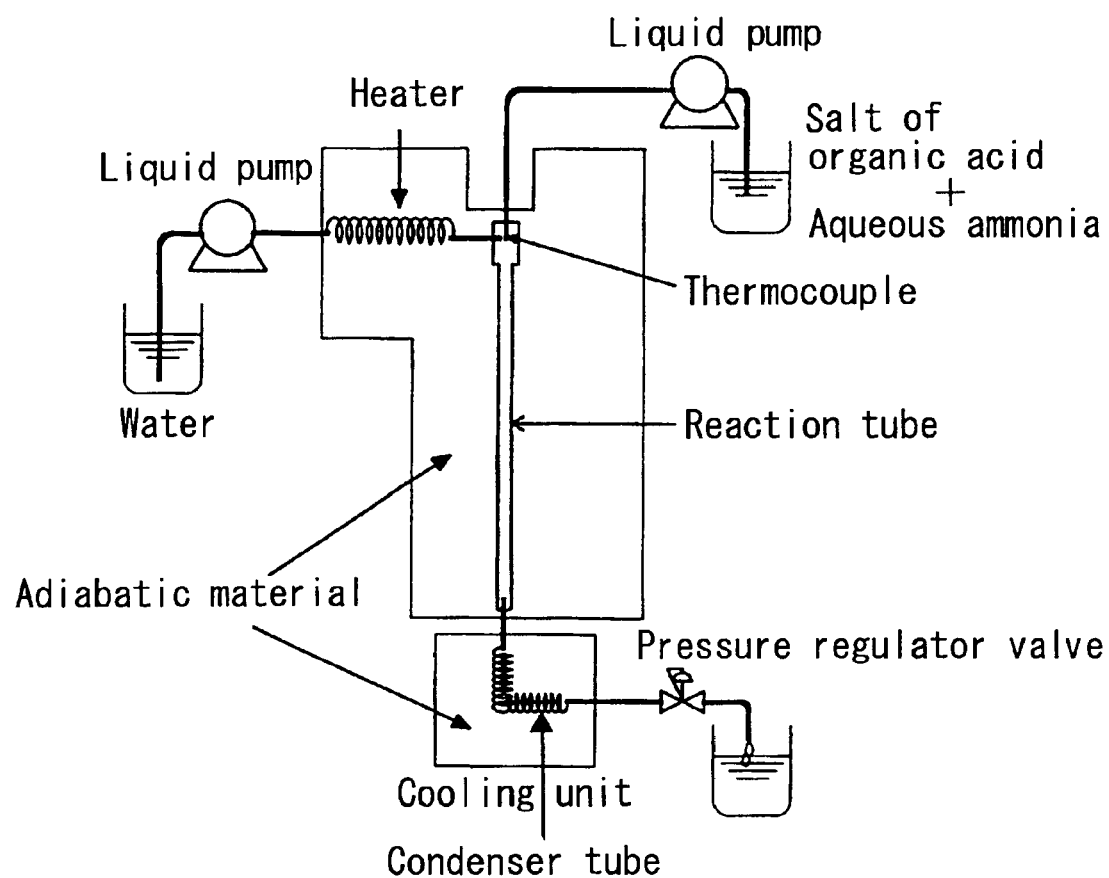
FIG. 1 is a flow sheet for a flow type of reaction apparatus equipped with two water pumps and used in the present invention.

Using the continuous reaction apparatus shown in FIG. 1, sodium lactate (reagent made by Wako Pure Chemicals) and aqueous ammonia (reagent chemicals made by Wako Pure Chemicals) were reacted under high-temperature and high-pressure water conditions in which the temperature was 374° C., the pressure was 30 MPa, and the density was 0.558 g/cm$^3$, to attempt the continuous synthesis of alanine by the introduction of amino groups.

The reactor was made from alloy C-276, the inside diameter of the reactor was 0.65 mm, and the reactor length was 25 cm. The reactor volume was therefore calculated to be 0.083 cm$^3$. A high-pressure injection pump was used to introduce the various preparations. The water used in the reaction was distilled water, and carrier water from which dissolved oxygen had been purged by bubbling with nitrogen gas was sent through the system at a rate of 9.3 mL/min. Using similarly treated distilled water, a substrate solution containing 1.08 M sodium lactate and 5 M aqueous ammonia was prepared, and this substrate solution was introduced into the reactor at a flow rate of 4.5 mL/min. The concentrations of the substrates prior to entering the reactor were 0.352 M for sodium lactate and 1.630 M for aqueous ammonia, and the reaction time was 0.201 second. The aqueous solution obtained after the reaction was examined with a high performance liquid chromatography/mass spectroscopy apparatus, which confirmed that an amino group had been introduced into the lactic acid, and that alanine had been produced. The alanine concentration was 6.6 mM, and the reaction yield thereof was 1.9%.

EXAMPLE 2

Sodium lactate and aqueous ammonia were continuously reacted for one hour using the same continuous reaction apparatus as in Example 1 and under exactly the same conditions. The reaction solution thus obtained was passed through a cation exchange resin (50W-X8, made by Dow Chemical) column, which separated the produced alanine from the sodium lactate and lactic acid, and the alanine-containing solution was concentrated and refined, after which it was precipitated with ethanol, and the precipitate was filtered and dried to obtain 0.47 g of the product of the present invention. This product was in the form of a pure-white powder, and was confirmed from FTIR absorption spectrum measurement results and NMR measurement results to be high-purity alanine containing substantially no impurities.

EXAMPLE 3

Figure 2:
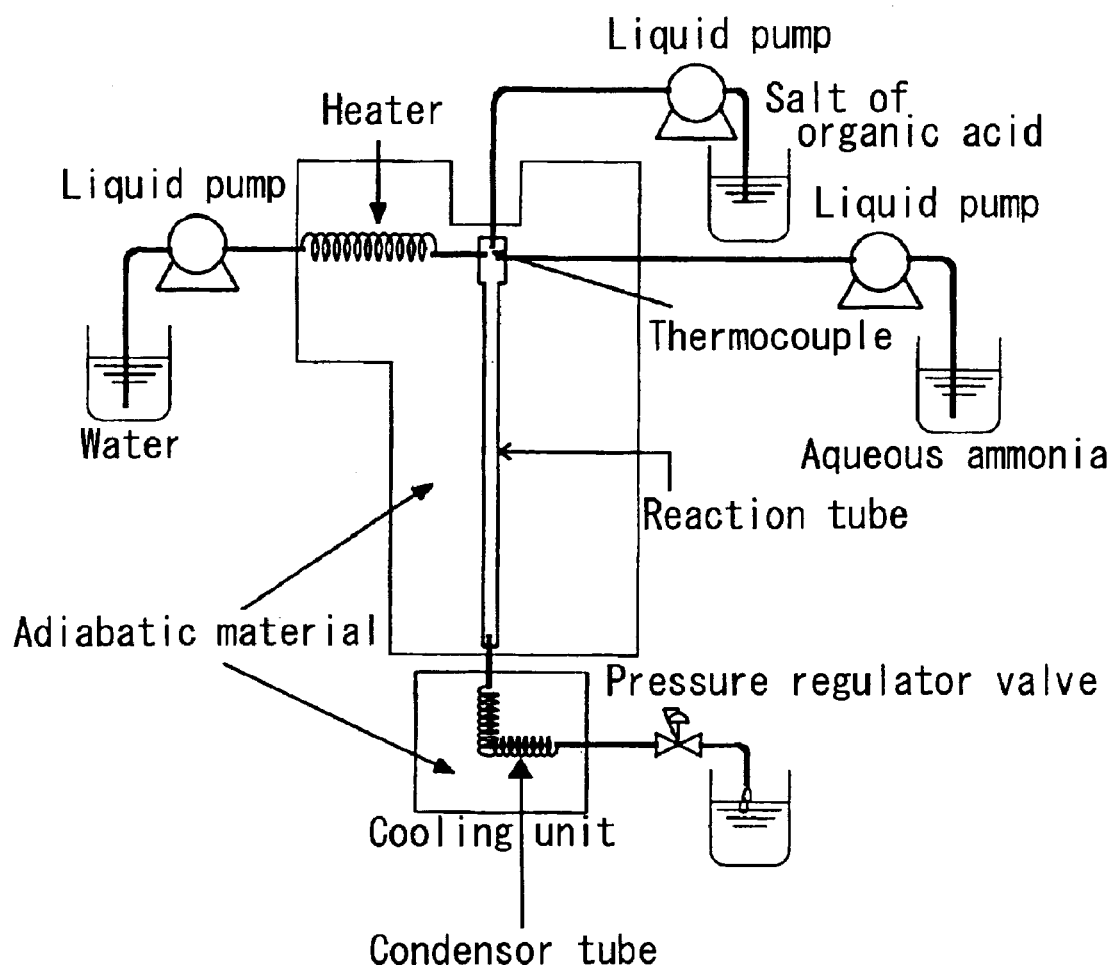
FIG. 2 is a flow sheet for a flow type of reaction apparatus equipped with three water pumps and used in the present invention.

The continuous synthesis of alanine from sodium lactate and aqueous ammonia was attempted by conducting the same reaction as in Example 1. Also, using the continuous reaction apparatus shown in FIG. 2, 1.08 M sodium lactate and 5 M ammonia aqueous solution that had each been separately prepared were injected into the reactor by two different water pumps. The reactor was made from alloy C-276, the inside diameter of the reactor was 0.65 mm, the reactor length was 25 cm, and the reactor volume was calculated to be 0.083 cm$^3$. Each introduced preparation was injected at a different flux by a high-pressure pump, which allowed the concentration ratio to be controlled as desired.

Some of the reaction conditions, however, were changed as follows.

Changed Reaction Conditions
  Reaction temperature: 383° C.
  High-temperature and high-pressure water density: 0.504 g/cm$^3$
  Carrier water flow rate: 10 mL/min
  1.08 M sodium lactate aqueous solution flow rate: 1.7 mL/min
  5 M ammonia aqueous solution flow rate: 2.5 mL/min The concentrations of the substrates prior to entering the reactor were 0.129 M for sodium lactate and 0.880 M for aqueous ammonia. The reaction time was 0.177 second, and the aqueous solution obtained after the reaction was examined with a high performance liquid chromatography/mass spectroscopy apparatus, which confirmed that an amino group had been introduced into the lactic acid, and that alanine had been produced. The alanine concentration was 3.1 mM, and the reaction yield thereof was 2.4%.

EXAMPLE 4

The continuous synthesis of alanine from sodium lactate and aqueous ammonia was attempted by conducting the same reaction as in Example 1. Some of the reaction conditions, however, were changed as follows.

Changed Reaction Conditions
  Reaction pressure: 35 MPa
  High-temperature and high-pressure water density: 0.588 g/cm$^3$
  Carrier water flow rate: 1.4 mL/min
  Substrate solution flow rate: 0.6 mL/min The concentrations of the substrates prior to entering the reactor were 0.324 M for sodium lactate and 1.5 M for aqueous ammonia. The reaction time was 1.464 seconds, and the aqueous solution obtained after the reaction was examined with a high performance liquid chromatography/mass spectroscopy apparatus, which confirmed that an amino group had been introduced into the lactic acid, and that alanine had been produced. The alanine concentration was 15.3 mM, and the reaction yield thereof was 4.7%.

COMPARATIVE EXAMPLE

The continuous synthesis of alanine from sodium lactate and aqueous ammonia was attempted by conducting the same reaction as in Example 1. Some of the reaction conditions, however, were changed as follows.

Changed Reaction Conditions
  Reaction temperature: 200° C.
  Reaction pressure: 15 MPa
  High-temperature and high-pressure water density: 0.8746 g/cm$^3$
  Carrier water flow rate: 2.6 mL/min
  Substrate solution flow rate: 4.5 mL/min The concentrations of the substrates prior to entering the reactor were 0.685 M for sodium lactate and 3.169 M for aqueous ammonia. The reaction time was 0.613 second, and the aqueous solution obtained after the reaction was examined with a high performance liquid chromatography/mass spectroscopy apparatus, which revealed that no alanine whatsoever had been obtained.

EXAMPLE 5

The continuous synthesis of alanine from sodium lactate and aqueous ammonia was attempted by conducting the same reaction as in Example 1. Some of the reaction conditions, however, were changed as follows.

Changed Reaction Conditions
  Reaction pressure: 25 MPa
  High-temperature and high-pressure water density: 0.4851 g/cm$^3$
  Carrier water flow rate: 6.7 mL/min
  Substrate solution flow rate: 2 mL/min The concentrations of the substrates prior to entering the reactor were 0.248 M for sodium lactate and 1.149 M for aqueous ammonia. The reaction time was 0.278 second, and the aqueous solution obtained after the reaction was examined with a high performance liquid chromatography/mass spectroscopy apparatus, which confirmed that an amino group had been introduced into the lactic acid, and that alanine had been produced. The alanine concentration was 4.0 mM, and the reaction yield thereof was 1.6%.

EXAMPLE 6

The continuous synthesis of alanine from sodium lactate and ammonium carbonate (reagent chemicals made by Kokusan Chemical) was attempted by conducting the same reaction as in Example 1. A 4.630 M ammonium carbonate aqueous solution was prepared using distilled water from which dissolved oxygen had been removed, and this was used as the carrier water. A 1.08 M sodium lactate substrate solution was prepared using distilled water from which dissolved oxygen had been removed, and this was supplied to the reaction. Some of the reaction conditions, however, were changed as follows.

Changed Reaction Conditions
  Reaction temperature: 300° C.
  Reaction pressure: 35 MPa
  High-temperature and high-pressure water density: 0.758 g/cm$^3$
  Carrier water flow rate: 4.5 mL/min
  Substrate solution flow rate: 4.5 mL/min The concentrations of the substrates prior to entering the reactor were 0.540 M for sodium lactate and 2.315 M for ammonium carbonate. The reaction time was 0.419 second, and the aqueous solution obtained after the reaction was examined with a high performance liquid chromatography/mass spectroscopy apparatus, which confirmed that an amino group had been introduced into the lactic acid, and that alanine had been produced. The alanine concentration was 1.9 mM, and the reaction yield thereof was 0.4%.

EXAMPLE 7

The continuous synthesis of alanine from sodium lactate and ammonium carbonate was attempted by conducting the same reaction as in Example 6. Some of the reaction conditions, however, were changed as follows.

Changed Reaction Conditions
  Reaction temperature: 400° C.
  Reaction pressure: 25 MPa
  High-temperature and high-pressure water density: 0.1486 g/cm$^3$ Carrier water flow rate: 18 mL/min
Substrate solution flow rate: 2 mL/min The concentrations of the substrates prior to entering the reactor were 0.108 M for sodium lactate and 0.463 M for ammonium carbonate. The reaction time was 0.037 second, and the aqueous solution obtained after the reaction was examined with a high performance liquid chromatography/mass spectroscopy apparatus, which confirmed that an amino group had been introduced into the lactic acid, and that alanine had been produced. The alanine concentration was 0.8 mM, and the reaction yield thereof was 0.7%.

EXAMPLE 8

The continuous synthesis of alanine from sodium lactate and ammonium carbonate was attempted by conducting the same reaction as in Example 6. Some of the reaction conditions, however, were changed as follows.
Changed Reaction Conditions
Reaction temperature: 374° C.
Reaction pressure: 40 MPa
High-temperature and high-pressure water density: 0.6090 g/cm$^3$
Carrier water flow rate: 3.5 mL/min
Substrate solution flow rate: 1 mL/min The concentrations of the substrates prior to entering the reactor were 0.240 M for sodium lactate and 1.029 M for ammonium carbonate. The reaction time was 0.674 second, and the aqueous solution obtained after the reaction was examined with a high performance liquid chromatography/mass spectroscopy apparatus, which confirmed that an amino group had been introduced into the lactic acid, and that alanine had been produced. The alanine concentration was 6.9 mM, and the reaction yield thereof was 2.9%.

EXAMPLE 9

The continuous synthesis of alanine from sodium lactate and ammonium acetate (reagent chemicals made by Wako Pure Chemicals) was attempted by conducting the same reaction as in Example 1. A substrate solution containing 0.10 M sodium lactate and 0.15 M ammonium acetate aqueous solution was prepared using distilled water from which dissolved oxygen had been removed, and this was supplied to the reaction. Some of the reaction conditions, however, were changed as follows.
Changed Reaction Conditions
Reaction temperature: 383° C.
High-temperature and high-pressure water density: 0.504 g/cm$^3$
Carrier water flow rate: 10 mL/min
Substrate solution flow rate: 3.9 mL/min The concentrations of the substrates prior to entering the reactor were 0.028 M for sodium lactate and 0.042 M for ammonium acetate aqueous solution. The reaction time was 0.181 second, and the aqueous solution obtained after the reaction was examined with a high performance liquid chromatography/mass spectroscopy apparatus, which confirmed that an amino group had been introduced into the lactic acid, and that alanine had been produced. The alanine concentration was 0.6 mM, and the reaction yield thereof was 2.1%.

EXAMPLE 10

The continuous synthesis of aspartic acid from sodium malate and aqueous ammonia was attempted by conducting the same reaction as in Example 1. A substrate solution containing 0.597 M sodium malate and 6.405 M aqueous ammonia was prepared using distilled water from which dissolved oxygen had been removed, and this was supplied to the reaction. Some of the reaction conditions, however, were changed as follows.
Changed Reaction Conditions
Reaction temperature: 383° C.
High-temperature and high-pressure water density: 0.504 g/cm$^3$
Carrier water flow rate: 10 mL/min
Substrate solution flow rate: 3.9 mL/min The concentrations of the substrates prior to entering the reactor were 0.168 M for sodium malate and 1.797 M for aqueous ammonia. The reaction time was 0.181 second, and the aqueous solution obtained after the reaction was examined with a high performance liquid chromatography/mass spectroscopy apparatus, which confirmed that an amino group had been introduced into the malic acid, and that aspartic acid had been produced. The aspartic acid concentration was 4.2 mM, and the reaction yield thereof was 2.5%.

EXAMPLE 11

The continuous synthesis of glycine from sodium glycolate (first-class reagent made by Wako Pure Chemicals) and aqueous ammonia was attempted by conducting the same reaction as in Example 1. A substrate solution containing 0.694 M sodium glycolate and 6.405 M aqueous ammonia was prepared using distilled water from which dissolved oxygen had been removed, and this was supplied to the reaction. Some of the reaction conditions, however, were changed as follows.
Changed Reaction Conditions
Reaction pressure: 25 MPa
High-temperature and high-pressure water density: 0.4851 g/cm$^3$
Carrier water flow rate: 6.7 mL/min
Substrate solution flow rate: 2.0 mL/min The concentrations of the substrates prior to entering the reactor were 0.160 M for sodium glycolate and 1.472 M for aqueous ammonia. The reaction time was 0.278 second, and the aqueous solution obtained after the reaction was examined with a high performance liquid chromatography/mass spectroscopy apparatus, which confirmed that an amino group had been introduced into the glycolic acid, and that glycine had been produced. The glycine concentration was 4.4 mM, and the reaction yield thereof was 2.8%.

EXAMPLE 12

The continuous synthesis of glycine from sodium glycolate and aqueous ammonia was attempted by conducting the same reaction as in Example 11. Some of the reaction conditions, however, were changed as follows.
Changed Reaction Conditions
Reaction temperature: 400° C.
Reaction pressure: 40 MPa
High-temperature and high-pressure water density: 0.5237 g/cm$^3$
Carrier water flow rate: 6 mL/min
Substrate solution flow rate: 1 mL/min The concentrations of the substrates prior to entering the reactor were 0.099 M for sodium glycolate and 0.915 M for aqueous ammonia. The reaction time was 0.373 second, and the aqueous solution obtained after the reaction was examined with a high performance liquid chromatography/mass spectroscopy apparatus, which confirmed that an amino group had been introduced into the glycolic acid, and that glycine had been produced. The glycine concentration was 5.4 mM, and the reaction yield thereof was 5.5%.

EXAMPLE 13

The continuous synthesis of 4-amino-n-butyric acid from sodium 4-hydroxy-n-butyrate (reagent made by Tokyo Chemical) and aqueous ammonia (reagent chemicals made by Wako Pure Chemicals) was attempted by conducting the same reaction as in Example 1. A substrate solution containing 0.77 M sodium 4-hydroxy-n-butyrate and 5 M aqueous ammonia was prepared and supplied to the reaction. Some of the reaction conditions, however, were changed as follows.

Changed Reaction Conditions
  Reaction temperature: 383° C.
  High-temperature and high-pressure water density: 0.5040 g/cm$^3$
  Carrier water flow rate: 10 mL/min
  Substrate solution flow rate: 3.9 mL/min The concentrations of the substrates prior to entering the reactor were 0.216 M for sodium 4-hydroxy-n-butyrate and 1.403 M for aqueous ammonia. The reaction time was 0.181 second, and the aqueous solution obtained after the reaction was examined with a high performance liquid chromatography/mass spectroscopy apparatus, which confirmed that an amino group had been introduced into the 4-hydroxy-n-butyric acid, and that 4-amino-n-butyric acid had been produced. The 4-amino-n-butyric acid concentration was 4.2 mM, and the reaction yield thereof was 1.9%.

EXAMPLE 14

The continuous synthesis of α,β-diaminosuccinic acid from sodium potassium (+)-tartrate (reagent chemicals made by Wako Pure Chemicals) and aqueous ammonia was attempted by conducting the same reaction as in Example 1. A substrate solution containing 0.57 M sodium potassium (+)-tartrate and 5 M aqueous ammonia was prepared using distilled water from which dissolved oxygen had been removed, and this was supplied to the reaction. Some of the reaction conditions, however, were changed as follows.

Changed Reaction Conditions
  Reaction temperature: 383° C.
  High-temperature and high-pressure water density: 0.504 g/cm$^3$
  Carrier water flow rate: 10 mL/min
  Substrate solution flow rate: 3.9 mL/min The concentrations of the substrates prior to entering the reactor were 0.160 M for sodium potassium tartrate and 1.403 M for aqueous ammonia. The reaction time was 0.181 second, and the aqueous solution obtained after the reaction was examined with a high performance liquid chromatography/mass spectroscopy apparatus, which confirmed that two amino groups had been introduced into the tartaric acid, and that α,β-diaminosuccinic acid had been produced. The α,β-diaminosuccinic acid concentration was 2.0 mM, and the reaction yield thereof was 1.3%.

EXAMPLE 15

The continuous synthesis of ethyl 3-amino-n-butyrate from sodium potassium ethyl 3-hydroxy-n-butyrate (reagent made by Tokyo Chemical) and aqueous ammonia was attempted by conducting the same reaction as in Example 1. A substrate solution containing 0.694 M ethyl 3-hydroxy-n-butyrate and 5 M aqueous ammonia was prepared using distilled water from which dissolved oxygen had been removed, and this was supplied to the reaction.

The concentrations of the substrates prior to entering the reactor were 0.226 M for ethyl 3-hydroxy-n-butyrate and 1.630 M for aqueous ammonia. The reaction time was 0.201 second, and the aqueous solution obtained after the reaction was examined with a high performance liquid chromatography/mass spectroscopy apparatus, which confirmed that an amino group had been introduced into the ethyl 3-hydroxy-n-butyrate, and that ethyl 3-amino-n-butyrate had been produced. The ethyl 3-amino-n-butyrate concentration was 3.3 mM, and the reaction yield thereof was 1.5%.

EXAMPLE 16

Figure 3:
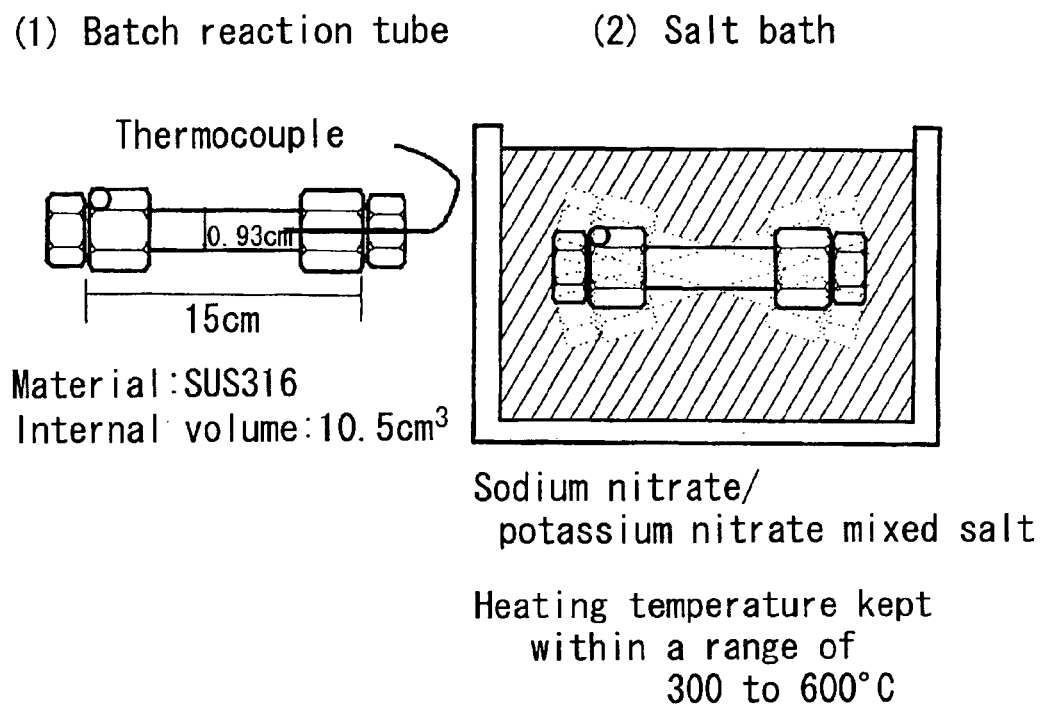
FIG. 3 shows the main components of a batch reaction tube used in a batch reaction, and a stirred salt bath that makes use of a sodium nitrate/potassium nitrate mixed salt.

The introduction of an amino group into lactic acid was attempted under high-temperature and high-pressure water conditions using sodium lactate and aqueous ammonia as the reaction substrates. The reaction was conducted in a batch reaction apparatus equipped with shaking and stirring means during the reaction, as shown in FIG. 3. A reaction tube with an internal volume of 10.5 cm$^3$ was used as the reactor, the temperature was set to 350° C. and the pressure to 30 MPa, and the reaction tube was put into a sodium nitrate/potassium nitrate mixed salt bath for 60 seconds to conduct an amino group introduction reaction. It took 20 seconds for the system to rise to the reaction temperature, and the reaction time was 40 seconds. The sodium lactate concentration in the reaction solution prior to reaction was 1.085 M, and the aqueous ammonia concentration was 5.002 M. The aqueous solution obtained after the reaction was examined with a high performance liquid chromatography/mass spectroscopy apparatus, which confirmed that 12.8 mM alanine had been produced. The reaction yield of alanine was 1.2%.

INDUSTRIAL APPLICABILITY

As detailed above, the present invention relates to a method for introducing an amino group, wherein an amino group is introduced into an organic acid or an organic ester by reacting an organic salt or an organic ester with ammonia or an ammonium salt compound under high-temperature and high-pressure water conditions, and to a method for synthesizing an amino acid, wherein an organic salt or an organic ester and ammonia or an ammonium salt compound are reacted under high-temperature and high-pressure water conditions, and an amino acid or an amino ester is synthesized from the organic salt or organic ester. The present invention affords the following effects: 1) A novel amino group introduction method that is conducted under high temperature and high pressure can be provided. 2) An amino acid or an amino ester can be synthesized by reacting an organic salt or an organic ester with ammonia or an ammonium salt compound under high temperature and high pressure. 3) An amino acid or an amino ester can be continuously synthesized at high speed from an organic salt or an organic ester by applying the above-mentioned amino group introduction method to a flow system. 4) An amino acid synthesis method that makes no use whatsoever of organic solvents or catalysts can be provided. 5) A high-purity amino acid compound can be manufactured. 6) The present invention is a chemical substance production system that is safe for the environment.

What is claimed is:

1. A method for introducing an amino group comprising introducing an amino group into an organic ester in a reaction time from 0.001 second to 10 minutes by reacting the organic ester with ammonia or an ammonium salt compound under high-temperature and high-pressure water conditions that the temperature is at least 250° C. and the pressure is at least 20 MPa.

2. A method for synthesizing an amino acid compound comprising reacting an organic ester with ammonia or an ammonium salt compound for a reaction time from 0.001 to second to 10 minutes under high-temperature and high-pressure water conditions that the temperature is at least 250° C. and the pressure is at least 20 MPa.

3. The method for synthesizing the amino acid according to claim 2, wherein the organic ester is reacted with aqueous ammonia, ammonium carbonate, or ammonium acetate.

4. The method for synthesizing the amino acid compound according to claim 2, wherein a hydroxy ester is the organic ester.

5. The method for synthesizing the amino acid compound according to claim 2, wherein an ester compound of lactic acid, glycolic acid, malic acid, tartaric acid, 3-hydroxy-n-butyric acid, or 4-hydroxy-n-butyric acid is the organic ester.

6. The method for synthesizing the amino acid compound according to claim 2, wherein the organic ester and the ammonia or the ammonium salt compound are introduced into a reactor and continuously reacted for a reaction time of from 0.01 second to 5 minutes under high-temperature and high-pressure water conditions.

7. A method for manufacturing an amino acid compound using an organic ester and ammonia or an ammonium salt compound as the reaction substrates under high-temperature and high-pressure water conditions that the temperature is at least 250° C. and the pressure is at least 20 MPa comprising introducing the organic ester and the ammonia or the ammonium salt compound into a reactor, reacting them continuously for a reaction time of from 0.01 second to 5 minutes under high-temperature and high-pressure water conditions, and then subjecting the reaction solution thus obtained to an ion exchange resin to obtain a separated and refined amino acid.

8. The method for synthesizing the amino acid compound according to claim 3, wherein a hydroxy ester is the organic ester.

9. The method for synthesizing the amino acid compound according to claim 3, wherein an ester compound of lactic acid, glycolic acid, malic acid, tartaric acid, 3-hydroxy-n-butyric acid, or 4-hydroxy-n-butyric acid is the organic ester.

10. The method for synthesizing the amino acid compound according to claim 4, wherein an ester compound of lactic acid, glycolic acid, malic acid, tartaric acid, 3-hydroxy-n-butyric acid, or 4-hydroxy-n-butyric acid is the organic ester.

11. The method for synthesizing the amino acid compound according to claim 8, wherein an ester compound of lactic acid, glycolic acid, malic acid, tartaric acid, 3-hydroxy-n-butyric acid, or 4-hydroxy-n-butyric acid is the organic ester.

12. The method for synthesizing the amino acid compound according to claim 3, wherein the organic ester and the ammonia or the ammonium salt compound are introduced into a reactor and continuously reacted for a reaction time of from 0.01 second to 5 minutes under high-temperature and high-pressure water conditions.

13. The method for synthesizing the amino acid compound according to claim 4, wherein the organic ester and the ammonia or the ammonium salt compound are introduced into a reactor and continuously reacted for a reaction time of from 0.01 second to 5 minutes under high-temperature and high-pressure water conditions.

14. The method for synthesizing the amino acid compound according to claim 5, wherein the organic ester and the ammonia or the ammonium salt compound are introduced into a reactor and continuously reacted for a reaction time of from 0.01 second to 5 minutes under high-temperature and high-pressure water conditions.

15. The method for synthesizing the amino acid compound according to claim 8, wherein the organic ester and the ammonia or the ammonium salt compound are introduced into a reactor and continuously reacted for a reaction time of from 0.01 second to 5 minutes under high-temperature and high-pressure water conditions.

16. The method for synthesizing the amino acid compound according to claim 9, wherein the organic ester and the ammonia or the ammonium salt compound are introduced into a reactor and continuously reacted for a reaction time of from 0.01 second to 5 minutes under high-temperature and high-pressure water conditions.

17. The method for synthesizing the amino acid compound according to claim 10, wherein the organic ester and the ammonia or the ammonium salt compound are introduced into a reactor and continuously reacted for a reaction time of from 0.01 second to 5 minutes under high-temperature and high-pressure water conditions.

18. The method for synthesizing the amino acid compound according to claim 11, wherein the organic ester and the ammonia or the ammonium salt compound are introduced into a reactor and continuously reacted for a reaction time of from 0.01 second to 5 minutes under high-temperature and high-pressure water conditions.

* * * * *